(12) United States Patent
Marczyk

(10) Patent No.: US 8,292,154 B2
(45) Date of Patent: Oct. 23, 2012

(54) SURGICAL APPARATUS FOR APPLYING TISSUE FASTENERS

(75) Inventor: Stanislaw Marczyk, Stratford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 131 days.

(21) Appl. No.: 12/727,487

(22) Filed: Mar. 19, 2010

(65) Prior Publication Data

US 2010/0264192 A1 Oct. 21, 2010

Related U.S. Application Data

(60) Provisional application No. 61/169,924, filed on Apr. 16, 2009.

(51) Int. Cl.
*A61B 17/068* (2006.01)

(52) U.S. Cl. ............... 227/176.1; 227/175.1; 227/177.1; 227/178.1; 227/901; 227/902; 606/151; 606/152; 606/153; 606/154; 411/920

(58) Field of Classification Search ............... 227/175.1, 227/176.1–178.1, 901, 902; 606/151–154; 411/920
See application file for complete search history.

(56) References Cited

U.S. PATENT DOCUMENTS

| | | | |
|---|---|---|---|
| 3,595,201 A | 7/1971 | Oudenhoven | |
| 4,534,350 A | 8/1985 | Golden et al. | |
| 4,534,352 A | 8/1985 | Korthoff | |
| 4,548,202 A | 10/1985 | Duncan | |
| 4,573,469 A | 3/1986 | Golden et al. | |
| 4,610,250 A | 9/1986 | Green | |
| 4,627,437 A | 12/1986 | Bedi et al. | |
| 4,665,916 A * | 5/1987 | Green | 227/178.1 |
| 4,667,674 A | 5/1987 | Korthoff et al. | |
| 4,671,280 A | 6/1987 | Dorband et al. | |
| 4,693,248 A | 9/1987 | Failla | |
| 4,805,617 A | 2/1989 | Bedi et al. | |
| 4,994,073 A * | 2/1991 | Green | 606/220 |
| 5,258,008 A | 11/1993 | Wilk | |
| 5,258,012 A | 11/1993 | Luscombe et al. | |
| 5,282,829 A | 2/1994 | Hermes | |
| 5,423,858 A | 6/1995 | Bolanos et al. | |
| 5,478,354 A | 12/1995 | Tovey et al. | |
| 5,542,594 A * | 8/1996 | McKean et al. ............ | 227/178.1 |
| 5,593,423 A | 1/1997 | Person et al. | |

(Continued)

FOREIGN PATENT DOCUMENTS

EP 0872213 A2 10/1998

(Continued)

OTHER PUBLICATIONS

European Search Report for EP 10250787.8-2310 date of completion is Jul. 13, 2010 (3 pages).

*Primary Examiner* — Lindsay Low
*Assistant Examiner* — Michelle Lopez

(57) ABSTRACT

A surgical apparatus for applying tissue fasteners is provided. The surgical apparatus includes a handle assembly, an elongated body that extends from the handle assembly, and a tool assembly mounted on the end of the elongate body. The tool assembly includes a cartridge assembly for receiving the tissue fasteners and a housing assembly for receiving a looped member. The tool assembly is configured to advance the tissue fasteners into the looped member to secure tissue between the fasteners and the looped member.

22 Claims, 5 Drawing Sheets

U.S. PATENT DOCUMENTS

| | | | |
|---|---|---|---|
| 5,653,373 A * | 8/1997 | Green et al. | 227/175.1 |
| 5,833,695 A * | 11/1998 | Yoon | 606/139 |
| 6,592,596 B1 | 7/2003 | Geitz | |
| 6,695,866 B1 | 2/2004 | Kuehn et al. | |
| 6,726,705 B2 | 4/2004 | Peterson et al. | |
| 6,869,436 B2 | 3/2005 | Wendlandt | |
| 6,916,332 B2 | 7/2005 | Adams | |
| 6,962,594 B1 | 11/2005 | Thevenet | |
| 6,981,983 B1 | 1/2006 | Rosenblatt et al. | |
| 7,083,636 B2 | 8/2006 | Kortenbach | |
| 2002/0165562 A1 | 11/2002 | Grant et al. | |
| 2004/0073256 A1 | 4/2004 | Marchitto et al. | |
| 2004/0093029 A1 | 5/2004 | Zubik et al. | |
| 2004/0138705 A1 | 7/2004 | Heino et al. | |
| 2005/0177176 A1 | 8/2005 | Gerbi et al. | |
| 2006/0015144 A1 | 1/2006 | Burbank et al. | |
| 2006/0235469 A1 | 10/2006 | Viola | |
| 2007/0162073 A1 | 7/2007 | Geitz | |
| 2007/0250118 A1 | 10/2007 | Masini | |
| 2007/0276436 A1 | 11/2007 | Sonnenschein et al. | |
| 2008/0290134 A1 * | 11/2008 | Bettuchi et al. | 227/176.1 |
| 2009/0001122 A1 * | 1/2009 | Prommersberger et al. | 227/176.1 |

FOREIGN PATENT DOCUMENTS

| | | |
|---|---|---|
| EP | 1621141 A2 | 2/2006 |
| EP | 1769756 A1 | 4/2007 |
| EP | 1994890 A1 | 11/2008 |

* cited by examiner

SURGICAL APPARATUS FOR APPLYING TISSUE FASTENERS

CROSS-REFERENCE TO RELATED APPLICATION

The present application claims priority to and benefit from U.S. Provisional Application Ser. No. 61/169,924, filed Apr. 16, 2009, the disclosure of which is incorporated by reference herein in its entirety.

BACKGROUND

1. Technical Field

The present disclosure relates to surgical instruments for use in endoscopic surgery. More particularly, the present disclosure relates to a surgical apparatus for use applying tissue fasteners.

2. Background of Related Art

Surgical staplers and other surgical stapling apparatus for use in endoscopic procedures are known. Typically, a standard surgical staple includes a loading unit having a tool assembly for applying one or more rows of staples to tissue. The tool assembly includes a cartridge for holding the staples and an anvil for deforming the staples against. As with all conventional staplers, the height of the staples must be longer than the thickness of the tissue being stapled in order to permit the staples to be deformed and bite into the tissue. When thicker tissue is being stapled and/or more of a bite is desired from the staple, a longer staple is required. To accommodate the larger staple, a larger staple cartridge is required. The process of deforming the staple(s) further requires that the staple cartridge and anvil are sturdy enough to handle the forces generated when stapling tissue.

Therefore, it would be beneficial to have a surgical apparatus capable of applying tissue fasteners to tissue with reduced force. It would further be beneficial for the tissue fastener applying device to have a reduced profile for introduction through smaller ports and access assemblies.

SUMMARY

Accordingly, a surgical apparatus for applying tissue fasteners is provided. The surgical apparatus includes a handle assembly, an elongated body that extends from the handle assembly, and a tool assembly mounted on the end of the elongate body. The tool assembly includes a cartridge assembly for receiving the tissue fasteners and a housing assembly for receiving a looped member. The tool assembly is configured to advance the tissue fasteners into the looped member to secure tissue between the fasteners and the looped member.

In one embodiment, the plurality of fasteners are non-deformable. Each of the plurality of fasteners may include at least one leg. The at least one leg of each of the plurality of fasteners may not extend through the looped member. At least one leg of each of the plurality of fasteners may be of a length slightly longer then the thickness of the tissue being secured. The tissue fasteners may each include at least one hook portion for engaging the looped member. The tissue fasteners may be composed of biocompatible material. The looped member may also be composed of biocompatible material. Either or both of the tissue fasteners and looped member may be biodegradable.

Also provided is a method of securing tissue. The method includes the step of providing a surgical apparatus including a cartridge assembly and a housing assembly, wherein the cartridge assembly includes a plurality of fasteners and the housing assembly includes a looped member. The method further includes the steps of positioning tissue to be secured between the cartridge assembly and the housing assembly, and actuating the surgical apparatus to eject the fasteners through the tissue and into engagement with the looped member, wherein the plurality of fasteners engage the looped member in a loop and hook configuration. The plurality of fasteners may each include at least one leg, wherein the at least one leg is slightly longer than the tissue being secured. The plurality of fasteners and the looped member may be biocompatible. The plurality of fasteners and/or the looped member are absorbable.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
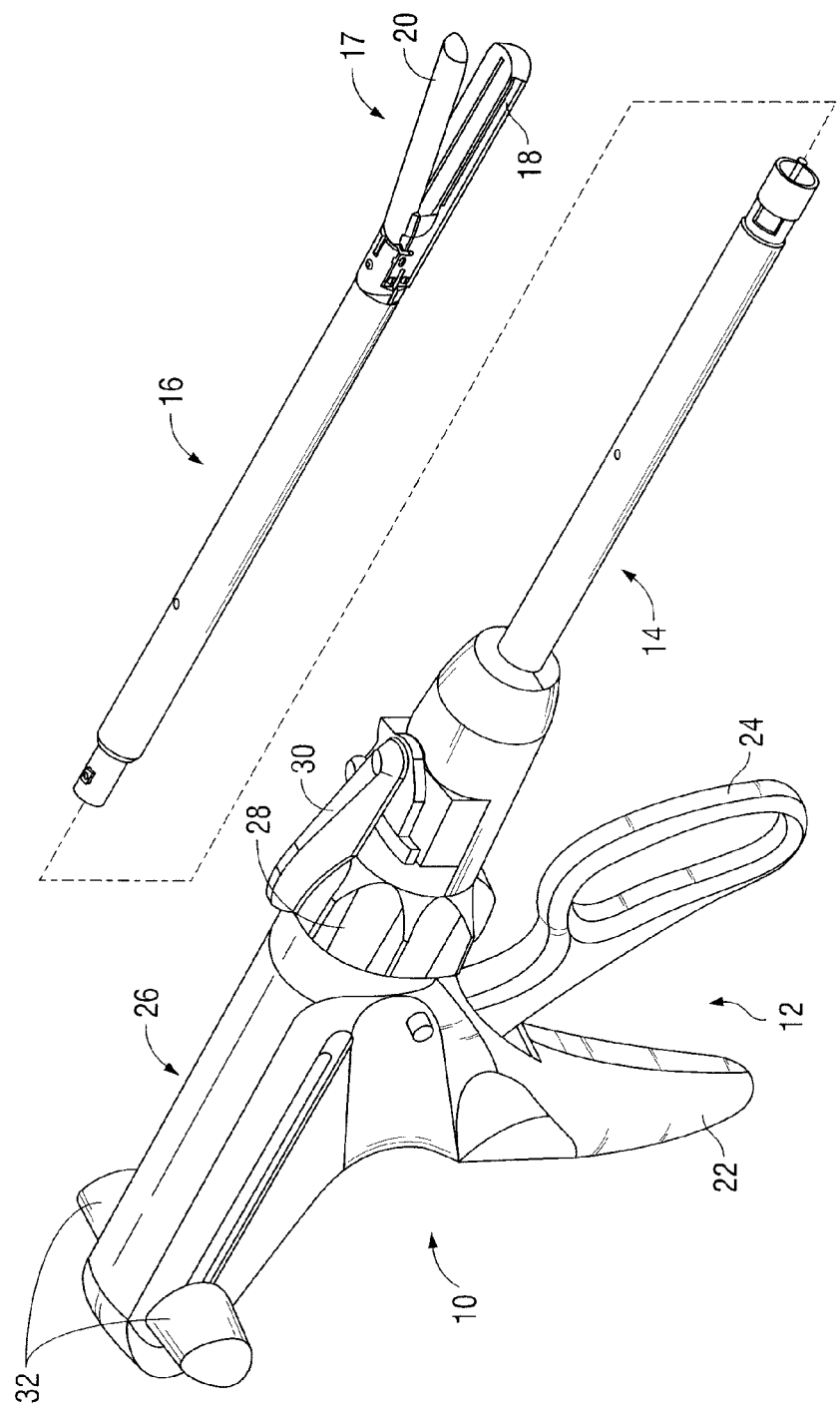
FIG. 1 is a perspective view of a surgical apparatus and a loading unit having a tool assembly.

Referring initially to FIG. 1, a surgical apparatus including an embodiment of the tool assembly of the present disclosure is shown generally as surgical apparatus 10. Although the tool assembly will be described as relates to surgical apparatus 10, the aspects of the present disclosure may be adapted for use with other surgical instruments.

With reference still to FIG. 1, briefly, surgical apparatus 10 includes a handle assembly 12 and an elongated body 14. Handle assembly 12 includes a stationary handle 22, a movable handle member 24, and a barrel portion 26. A rotatable member 28 is mounted on the distal end of barrel portion 26 to facilitate rotation of elongated body 14 with respect to handle assembly 12. An articulation lever 30 is also mounted on the distal end of barrel portion 26 adjacent rotatable knob 28 to facilitate articulation of a tool assembly 17 on a distal end of a loading unit 16. A pair of retraction knobs 32 is movably positioned along barrel portion 26 to return surgical stapling apparatus 10 to a retracted position.

The remainder of the description will provide a detailed discussion of loading unit 16, more particularly, tool assembly 17. For further discussion of the operation of handle assembly 12, please refer to commonly owned U.S. Pat. No. 7,303,107 to Milliman et al., the disclosure of which is incorporated by reference herein in its entirety. As noted above, the aspects of the present disclosure may be modified for use with other handle assemblies and actuation mechanisms, and therefore, should not be read as limited to the embodiments herein described.

Figure 2:
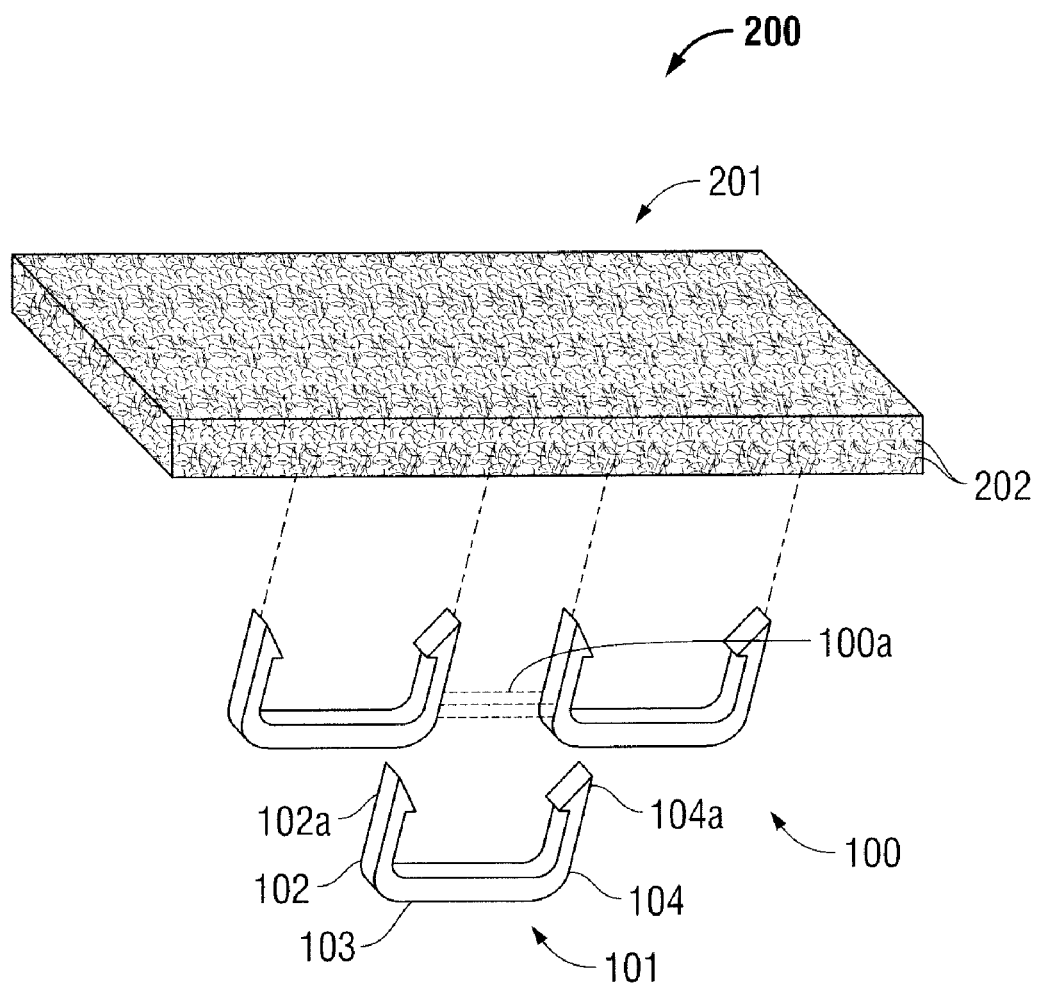
FIG. 2 is an enlarged perspective view of a plurality of tissue fasteners and a looped member according to an embodiment of the present disclosure.

Still referring to FIG. 1, loading unit 16 is releasably secured to a distal end of elongated body 14. Loading unit 16 includes tool assembly 17 having a cartridge assembly 18 and a housing assembly 20. In an alternative embodiment, tool assembly 17 is integrally formed with elongated body 14. Cartridge assembly 18 is configured to house a plurality of tissue fasteners or staple clips 100 (FIG. 2). Housing assembly 20 is movably secured in relation to cartridge assembly 18 and is configured to retain a looped member 200 (FIG. 2) adjacent to the plurality of staple clips 100.

Figure 3:
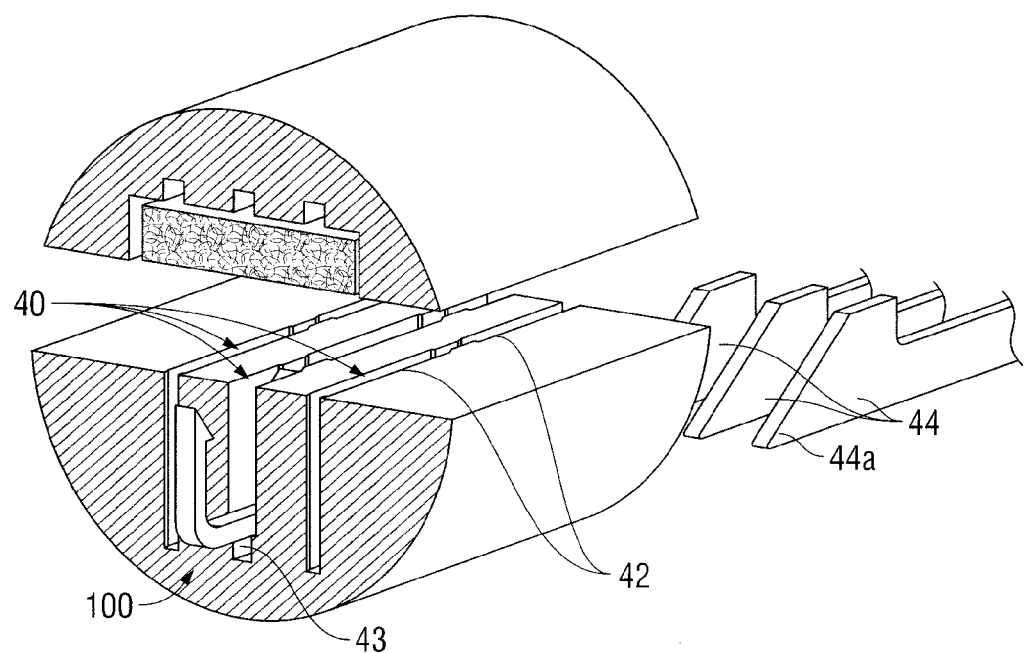
FIG. 3 is an enlarged partial cutaway perspective view of a portion of the tool assembly of FIG. 1.

With reference now to FIG. 2, tissue fasteners 100 include a substantially C-shaped member 101 defined a pair of legs 102, 104 extending from a base 103. Legs 102, 104 each include a hooked or barbed end 102a, 104a, respectively. As will be discussed in further detail below, hooked ends 102a, 104a are configured to engage loops 202 formed in looped member 200. As will also be discussed in greater detail below, base 103 is configured to engage a sled 44 (FIG. 3). Base 103 may include a thickened or reinforced portion or may be composed of a stronger or more dense material than legs 102, 104. Fasteners 100 are biocompatible and may be composed of metal, plastic, polymer or other suitable material. Fasteners 100 may also be absorbable. Fasteners 100 may be provided individually, either separate from or preloaded in cartridge assembly 18. Alternatively fasteners 100 may be provided as a plurality of connected fasteners including a bridge member 100a (shown in phantom) for facilitating loading of cartridge assembly 18. In one embodiment, bridge member 100a is configured to break away from fasteners 100 upon ejection of fasteners 100 from cartridge assembly 18. In an alternative embodiment, bridge members 100a remain attached to fasteners 100 after being ejected from cartridge assembly 18 and through tissue "T", thereby forming a more securely engagement with tissue "T".

Still referring to FIG. 2, looped member 200 includes a substantially planar member 201 defined by a plurality of loops 202. Loops 202 are configured to engage hooked ends 102a, 104a formed on legs 102, 104, respectively of fasteners 100. Looped member 200 may be formed of metal, plastic, polymer or other suitable material. Looped member 200 may be biocompatible and may also be absorbable. It is envisioned that looped member 200 may be coated or otherwise include a substance for more securely receiving hooked ends 102a, 104a of fastener 100. Looped member 200 may further include a disinfectant, antibacterial, wound therapy or other suitable substance for assisting in tissue healing and/or preventing infection.

Figure 4:
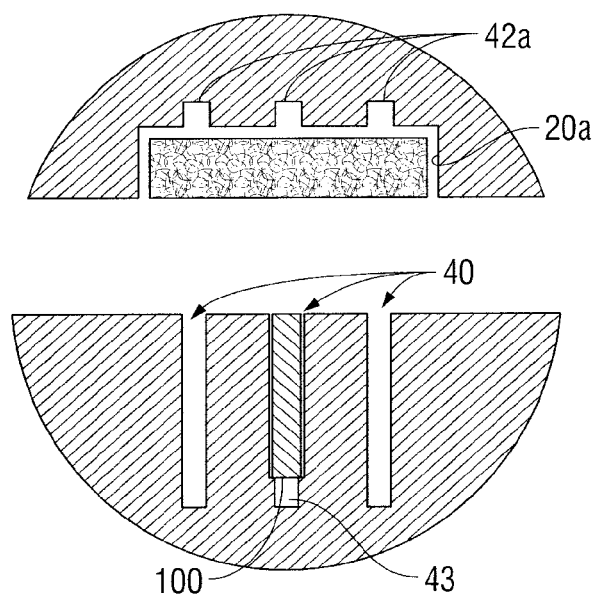
FIG. 4 is an enlarged cross-sectional end view of the tool assembly of FIGS. 1 and 3.

Turning now to FIGS. 3 and 4, cartridge assembly 18 includes a plurality of channels 40 configured to receive a plurality of fasteners 100. Although shown including three channels, it is envisioned that that cartridge assembly 18 may include any number of channels 40. Each of channels 40 includes one or more pockets 42 configured to receive fasteners 100. Pockets 42 may be aligned along channels 40, or instead may be staggered, as shown. Fasteners 100 may be received within pockets 42 individually, or, as described above, may be connected by a bridge member 100a (FIG. 2, shown in phantom). In some embodiments, fasteners 100 are provided preloaded within cartridge assembly 18. Alternatively, fasteners 100 are provided separate from cartridge assembly 18 and require loading by a clinician. In this manner, it is envisioned that cartridge assembly 18 may be reloaded after use and reused one or more times.

Still referring to FIGS. 3 and 4, each of channels 40 further includes a space 43 between cartridge assembly 18 and base portion 103 of fastener 100 configured to receive a proximal end 44a of a sled 44. Sleds 44 are configured to slide along respective channels 40 and engage bases 103 of fasteners 100. As noted above, engagement of sleds 44 with fasteners 100 causes the ejection of fasteners 100 from within pocket 42. In one embodiment, cartridge assembly 18 further includes a plurality of pushers (not shown) associated with each of fasteners 100. The pushers are configured to engage sleds 44 and aid in the ejecting of fasteners 100 by eliminating unnecessary force on fasteners 100.

With reference still to FIGS. 3 and 4, housing assembly 20 includes a recess 20a for receiving looped member 200. Recess 20a may be configured to receive looped members 200 of various dimensions and thickness. Looped member 200 is selectively received within recess 20a. It is envisioned that looped member 200 may be lightly glued or otherwise partially secured within recess 20a to prevent accidently release of looped member 200 prior to activation of surgical apparatus 10. Recess 20a may further include cut-outs 42a corresponding to channels 42 formed in cartridge assembly 18 to accommodate hooked ends 102a, 104a of fasteners 100 in the event fasteners 100 are configured to extend, partially (FIG. 5B) or fully (FIG. 5C), through looped member 200.

With reference now to FIGS. 1-5C, the operation of surgical apparatus 10, and tool assembly 18, in particular, will be described. Once surgical apparatus 10 has been manipulated to receive the tissue to be fastened between cartridge assembly 18 and housing assembly 20, movable handle member 24 of handle assembly 14 is moved towards stationary handle 22 to cause approximation of housing assembly 20 towards cartridge assembly 18, thereby securing tissue "T" therebetween. Continued movement of movable handle member 24 towards stationary handle 22 causes proximal advancement of sleds 44 through channels 40 formed in cartridge assembly 18. As sleds 44 pass through spaces 43 formed in channels 40, sleds 44 engage bases 103 of fasteners 100 and cause the ejection of fasteners 100 from cartridge assembly 18. As fasteners 100 are ejected from pockets 42 formed in cartridge assembly 18, legs 102, 104 of fasteners 100 pierce through tissue "T" (FIG. 5A) and hooked ends 102a, 104a of legs 102, 104, respectively, engage loops 202 of looped pad 200.

Unlike with a traditional staple that requires an anvil assembly for deforming the legs of the staple and legs that are longer than the thickness of the tissue being stapled, fasteners 100 do not require an anvil assembly because legs 102, 104 are not deformed, and therefore, may be of a shorter length. In this manner, cartridge assembly 18 of surgical apparatus 10 includes a smaller profile then a traditional stapler. Furthermore, the forces necessary to drive fasteners 100 through tissue "T" and into looped member 200 are less then that required to deform a traditional staple, therefore, cartridge assembly 18 and housing assembly 20 of surgical apparatus 10 may be constructed of lighter weight material and/or with fewer structural reinforcements, thereby further reducing the profile of tool assembly 17. The reduce profile of tool assembly 17 permits a clinician to use surgical apparatus 10 with ever smaller access assemblies, i.e. 5 mm access ports.

Figure 5A:
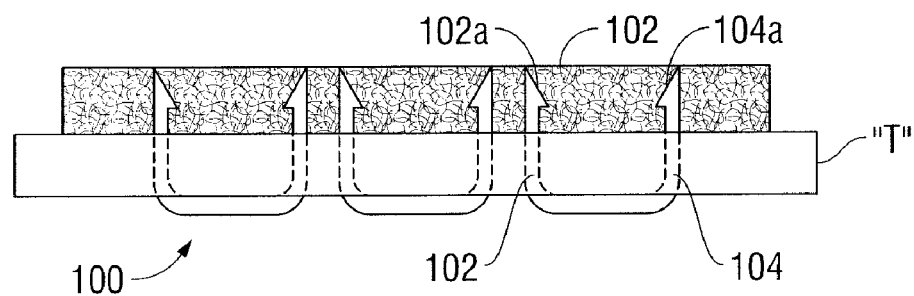
FIGS. 5A-C are side views of the fasteners and looped member of FIG. 2 in a first configuration (FIG. 5A), a second configuration (FIG. 5B) and a third configuration (FIG. 5C)
Figure 5B:
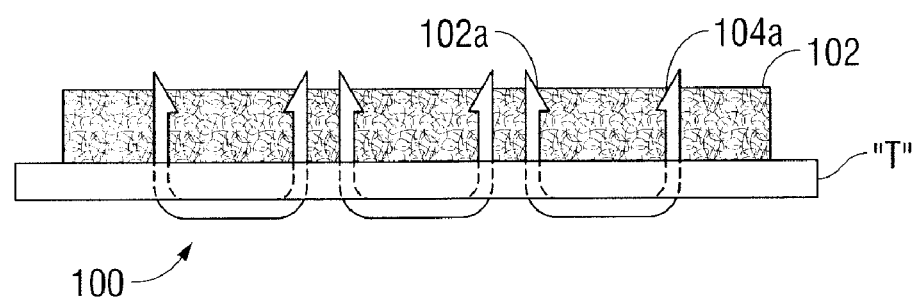
Figure 5C:
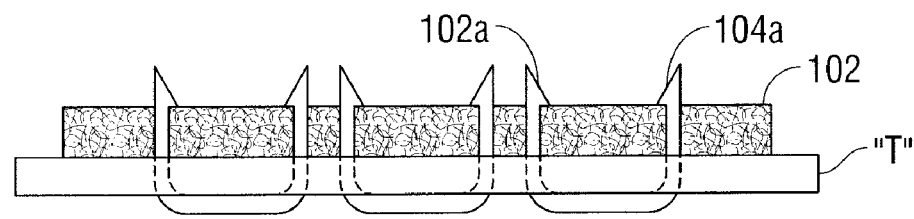

With reference now to FIGS. 5A-5C, the configuration in which hooked ends 102a, 104a of fasteners 100 engage looped member 200 may vary. Referring initially to FIG. 5A, in a first configuration, hooked ends 102a, 104a of fastener 100 are completely received within looped member 200. This may be accomplished by varying the length of legs 102, 104 of fastener 100 and/or by varying the thickness of looped member 200, relative to the thickness of tissue "T". Alternatively, in a second configuration, hooked ends 102a, 104a may be partially received through looped member 200 (FIG. 5B) or completely received through looped member 200 (FIG. 5C). In each of these configurations, hooked ends 102a, 104a of fastener 100 and loops 202 of looped member 202 are configured to prevent withdrawal of hooked ends 102a, 104a through looped member 202.

Figure 6:
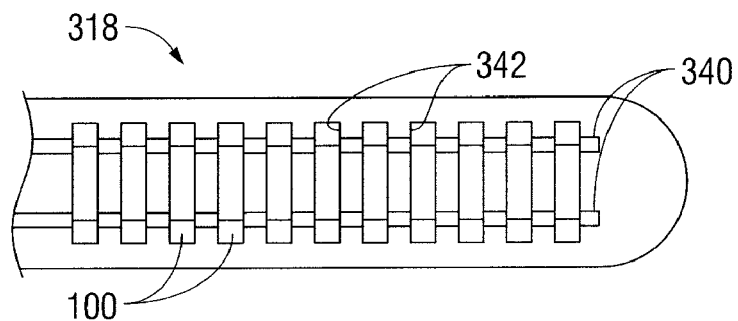
FIG. 6 is a top view of a cartridge assembly according to another embodiment of the present disclosure.

Turning now to FIG. 6, in an alternate embodiment, cartridge assembly 318 includes one or more channels 340 and a plurality of horizontally aligned pockets 342. Pockets 342 are configured to receive fasteners 100. Channels 340 are substantially similar to channels 40 described hereinabove and are configured to receive sled 44 (FIG. 3) therethrough. Passage of sleds 44 along channels 40 causes engagement of sleds 44 with fasteners 100 received within pockets 342, thereby ejecting fasteners 100 from cartridge assembly 318.

Figure 7:
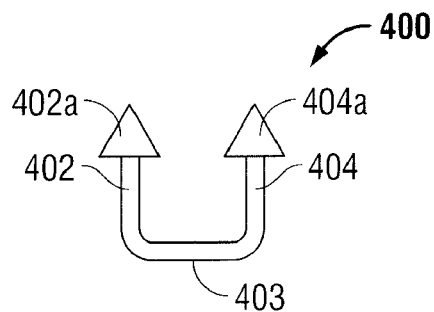
FIG. 7 is an enlarged side view of a tissue fastener according to an alternate embodiment of the present disclosure.
Figure 8:
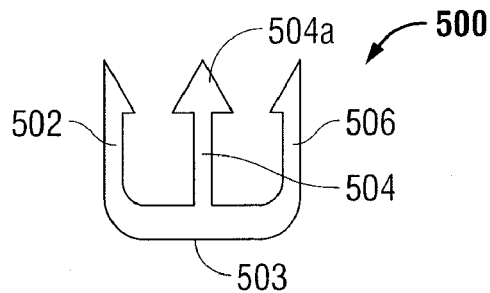
FIG. 8 is an enlarged side view of a tissue fastener according to another embodiment of the present disclosure.
Figure 9:
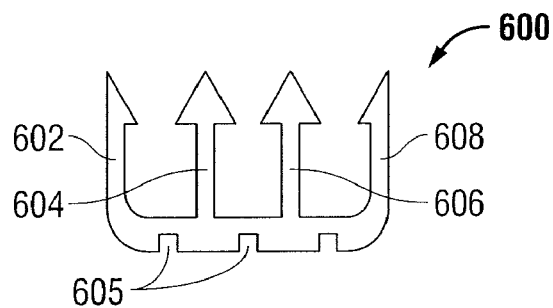
FIG. 9 is an enlarged side view of a tissue fastener according to still another embodiment of the present disclosure.

With reference now to FIGS. 7-9, alternate embodiments of tissue fastener 100 are shown. Referring initially to FIG. 7, tissue fastener 400 is substantially similar to tissue fastener 100 described hereinabove. Fastener 400 includes a base 403 and pair of legs 402, 404 each including conically shaped hooked portions 402a, 404b. With reference to FIG. 8, tissue fastener 500 includes three legs 502, 504, 506 extending from a widened or reinforced base 503. Central leg 504 includes a double hooked end 504a. Turning to FIG. 9, tissue fastener 600 includes a plurality of legs 602, 604, 606, 606 extending from a base 603. Base 603 of tissue fastener 600 includes a series of cutouts 605 configured to engage sleds 44 (FIG. 3) of tool assembly 17 (FIG. 1) as surgical apparatus 10 is actuated.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, in one embodiment, looped member 200 may be replaced by a slab of gel, mesh or other suitable material. In another embodiment, tool assembly 18 may be configured to further include a knife mechanism (not shown) for cutting or separating tissue that has been "stapled." In this manner, looped member 200 may be formed of separate pads or may instead be separated by the knife mechanism.

What is claimed is:

1. A surgical apparatus for applying tissue fasteners, comprising:
   a handle assembly;
   an elongated body extending from the handle assembly; and
   a tool assembly operably mounted on a distal end of the elongate body, the tool assembly including a cartridge assembly for receiving a plurality of fasteners and a housing assembly including a recess for receiving a looped member at least partially therein, wherein the tool assembly is configured to advance the plurality of fasteners into the looped member to secure tissue therebetween, wherein each of the plurality of fasteners includes at least one leg, and wherein no portion of any of the legs of the plurality of fasteners extends completely through the looped member.

2. The surgical apparatus of claim 1, wherein the plurality of fasteners are non-deformable.

3. The surgical apparatus of claim 1, wherein the plurality of fasteners each include at least one hook portion for engaging the looped member.

4. The surgical apparatus of claim 1, wherein the looped member is VELCRO.

5. The surgical apparatus of claim 1, wherein the fasteners are composed of biocompatible material.

6. The surgical apparatus of claim 1, wherein the looped member is composed of biocompatible material.

7. The surgical apparatus of claim 1, wherein the fasteners are biodegradable.

8. The surgical apparatus of claim 1, wherein the looped member is biodegradable.

9. The surgical apparatus of claim 1, wherein the cartridge assembly includes a plurality of channels for receiving the plurality of fasteners.

10. The surgical apparatus of claim 9, wherein the plurality of channels include a plurality of pockets for receiving the plurality of fasteners.

11. The surgical apparatus of claim 9, wherein each of the plurality of channels is configured to receive a sled for ejecting staples therefrom.

12. The surgical apparatus of claim 1, wherein the entire looped member is within the recess and is on a first side of a plane defined by a tissue-contacting surface of the housing assembly, and wherein the cartridge assembly is on a second side of the plane defined by a tissue-contacting surface of the housing assembly.

13. The surgical apparatus of claim 1, wherein the looped member includes a first lateral surface and a second lateral surface, wherein the plurality of fasteners each include at least one leg extending from a backspan, wherein the portion of each leg that is farthest from the backspan of each of the plurality of fasteners extends through the first lateral surface of the looped member, wherein the portion of each leg that is farthest from the backspan of each of the plurality of fasteners does not extend through the second lateral surface of the looped member.

14. The surgical apparatus of claim 13, wherein the first lateral surface of the looped member is substantially parallel to the second lateral surface of the looped member.

15. The surgical apparatus of claim 1, wherein the plurality of fasteners each include at least one leg extending from a backspan, wherein the portion of each leg that is farthest from the backspan of each of the plurality of fasteners does not extend through the looped member.

16. A method of securing tissue comprising the steps of:
   providing a surgical apparatus including a cartridge assembly and a housing assembly, wherein the cartridge assembly includes a plurality of fasteners and the housing assembly includes a recess for receiving a looped member at least partially therein, wherein the looped member includes a first lateral surface and a second lateral surface, wherein the plurality of fasteners each include at least one leg extending from a backspan, wherein the portion of each leg that is farthest from the backspan of each of the plurality of fasteners extends through the first lateral surface of the looped member, wherein the portion of each leg that is farthest from the backspan of each of the plurality of fasteners does not extend through the second lateral surface of the looped member;
   positioning tissue to be secured between the cartridge assembly and the housing assembly;
   actuating the surgical apparatus to eject the fasteners through the tissue and into engagement with the looped member, wherein the plurality of fasteners engage the looped member in a loop and hook configuration.

17. The method of claim 16, wherein the plurality of fasteners and the looped member are biocompatible.

18. The method of claim 16, wherein the plurality of fasteners are absorbable.

19. The method of claim 16, wherein the looped member is absorbable.

20. The method of claim 16, wherein the first lateral surface of the looped member is substantially parallel to the second lateral surface of the looped member.

21. The method of claim 16, wherein no portion of any of the legs of the plurality of fasteners extends completely through the looped member.

22. The method of claim 16, wherein the plurality of fasteners each include at least one leg extending from a backspan, wherein the portion of each leg that is farthest from the backspan of each of the plurality of fasteners does not extend through the looped member.

* * * * *